United States Patent
Baillard et al.

(10) Patent No.: US 9,797,829 B2
(45) Date of Patent: Oct. 24, 2017

(54) METHOD FOR ASSESSING THE DAMAGE TO A PAINT-COVERED COMPOSITE MATERIAL, MEASURING TWO SEPARATE CRITERIA ON THE SPECTROGRAM

(71) Applicant: AIRCELLE, Gonfreville l'Orcher (FR)

(72) Inventors: Andre Baillard, Bretteville du Grand Caux (FR); Odile Lefeu, La Remuee (FR); Frederic Joubert, Le Havre (FR); Emmanuel Piel, Le Havre (FR)

(73) Assignee: AIRCELLE, Gonfreville l'Orcher (FR)

( * ) Notice: Subject to any disclaimer, the term of this patent is extended or adjusted under 35 U.S.C. 154(b) by 0 days.

(21) Appl. No.: 15/098,895

(22) Filed: Apr. 14, 2016

(65) Prior Publication Data
US 2016/0231238 A1    Aug. 11, 2016

Related U.S. Application Data

(63) Continuation of application No. PCT/FR2014/052656, filed on Oct. 17, 2014.

(30) Foreign Application Priority Data

Oct. 17, 2013   (FR) ..................................... 13 60123

(51) Int. Cl.
*G01N 21/3563* (2014.01)
*G01N 25/72* (2006.01)
(Continued)

(52) U.S. Cl.
CPC ............ *G01N 21/3563* (2013.01); *G01J 3/28* (2013.01); *G01N 21/8422* (2013.01);
(Continued)

(58) Field of Classification Search
CPC .......... G01N 21/3563; G01N 21/8422; G01N 21/8851; G01N 25/72; G01N 33/32; G01J 3/28

See application file for complete search history.

(56) References Cited

U.S. PATENT DOCUMENTS 4,492,867 A    1/1985   Laarhoven et al.
6,184,528 B1   2/2001   DiMarzio et al.
(Continued)

FOREIGN PATENT DOCUMENTS

EP    2343531    7/2011
FR    2981157    4/2013

OTHER PUBLICATIONS

International Search Report for International Application PCT/FR2014/052656, dated Dec. 5, 2014.

*Primary Examiner* — David Porta
*Assistant Examiner* — Faye Boosalis
(74) *Attorney, Agent, or Firm* — Burris Law, PLLC

(57) ABSTRACT

A method for assessing damage to a composite material covered with a polyurethane-type paint is provided. Two separate criteria are measured on a spectrogram obtained by infrared spectrometry, thereby characterizing thermal ageing of the paint, each separate criteria being a measurement on a curve of a spectrum of the spectrogram of a height of a particular peak, thereby giving two independent assessments of the thermal ageing. Then, the two separate criteria are combined together in order to obtain a result of a level of the damage.

10 Claims, 4 Drawing Sheets

(51) Int. Cl.
*G01J 3/28* (2006.01)
*G01N 33/32* (2006.01)
*G01N 21/84* (2006.01)
*G01N 21/88* (2006.01)
*G01N 21/95* (2006.01)

(52) U.S. Cl.
CPC ......... *G01N 21/8851* (2013.01); *G01N 21/95* (2013.01); *G01N 25/72* (2013.01); *G01N 33/32* (2013.01); *G01J 2003/2859* (2013.01); *G01N 2021/8427* (2013.01); *G01N 2021/8472* (2013.01)

(56) References Cited

U.S. PATENT DOCUMENTS

| | | | | |
|---|---|---|---|---|
| 6,434,267 | B1 * | 8/2002 | Smith | G01J 3/46 374/1 |
| 6,903,339 | B2 * | 6/2005 | Shelley | G01B 11/0625 250/339.01 |
| 8,436,311 | B2 * | 5/2013 | Shelley | G01N 21/3563 250/340 |
| 2011/0001047 | A1 | 1/2011 | Shelley et al. | |
| 2011/0199098 | A1 | 8/2011 | Bense et al. | |

* cited by examiner

METHOD FOR ASSESSING THE DAMAGE TO A PAINT-COVERED COMPOSITE MATERIAL, MEASURING TWO SEPARATE CRITERIA ON THE SPECTROGRAM

CROSS-REFERENCE TO RELATED APPLICATIONS

This application is a continuation of International Application No. PCT/FR2014/052656, filed on Oct. 17, 2014, which claims the benefit of FR 13/60123, filed on Oct. 17, 2013. The disclosures of the above applications are incorporated herein by reference.

FIELD

The present disclosure relates to a method for assessing the damage to composite materials.

BACKGROUND

The statements in this section merely provide background information related to the present disclosure and may not constitute prior art.

Composite materials, in particular panels used in aeronautical applications, proximate to the engines, are intended for operation at temperatures below a maximum threshold. These panels, whether forming one single layer or used in a sandwich structure comprising a central core such as honeycomb covered with two external skins or face sheets, include unique mechanical characteristics and a reduced mass, and may take various shapes.

However, subsequent to thermal events comprising an increase of temperature above a maximum threshold, and depending on the exposure times, some damage to the materials of the panels may occur, which may reduce the structural strength characteristics. Thus, it is desirable to be able to characterize the level of the material damage during maintenance operations in order to increase safety.

In order to carry out inspection on these composite materials, it is known to apply a primary paint over the surface, in particular a polyurethane paint, which will undergo color transformations during thermal events.

A first known method for damage assessment consists in visually studying the discoloration of the primary paint in order to deduce therefrom some level of evolution of the material. This method gives a qualitative indication, but does not allow for an accurate quantitative measurement of the damage.

Another known non-destructive method, in particular presented by the documents EP-A1-2343531 and US-A1-20110001047, performs an analysis of the discoloration of a primary paint by a technique based on infrared spectrometry.

In particular, the second mentioned document presents the following method: after having carried out a calibration model, infrared radiation is emitted on a point of the surface of the material to be analyzed; then, the diffused reflection spectrum of this surface is measured; and by considering on this spectrum a criterion which is compared to the calibration model, a history of the thermal or chemical aspects of the coating is assessed, in order to deduce therefrom a condition of the composite material supporting it.

Nonetheless, this method is complex to carry out, and the obtained results highly depend on the implementation of the primary paint. In particular, thickness variations of the coating layer, of its polymerization cycle, of the number of deposited layers or of the surface condition, will disturb the infrared reflection. The results as well as the conclusions related to the damage to the material are not accurate.

Other known non-destructive methods for assessing the damage to the materials use in particular ultrasonic or thermographic conventional techniques which allow in particular detecting detachments between the layers of the materials. Thus, it is possible, for example, to control the detachment between the skin and the core of a panel comprising a sandwich structure. Nonetheless, this method does not allow assessing the condition of the material by itself.

SUMMARY

In one form, the present disclosure provides a method for assessing damage to a composite material covered with a polyurethane-type paint, using an infrared spectrometry of the paint, remarkable in that on the obtained spectrogram, two separate criteria characterizing the thermal ageing of the paint are measured, each comprising the measurement, on the curve of the spectrum, of a height of a particular peak, giving two independent assessments of this ageing, then these two criteria are combined together in order to obtain a result of the level of the damage.

One advantage of this assessment method is that, in a rapid and economical manner, the simultaneous comparison of the two combined criteria allows addressing the variations of the parameters of implementation of the paint and of the measurement conditions, which gives an accurate assessment of the material damage.

The damage assessment method according to the present disclosure moreover may include one or more of the following characteristics, which may be combined together.

Advantageously, in order to obtain a first criterion, the height of the particular peak is measured relative to a base line passing through the first two immediately adjacent troughs at each side of this peak.

Advantageously, in order to obtain a second criterion, the height of the particular peak is measured relative to a base line passing through the first two significant troughs on each side of this peak.

Advantageously, the two criteria are disposed along the two axes of a graph in order to combine them, this graph comprising areas separated by limits which determine the level of thermal degradation of the material. Thus, a damage assessment is achieved.

In particular, the graph may include a first area corresponding to an absence of evolution of the chemical structure of the material, a second area corresponding to an evolution of this structure resulting in a low damage, and a third area corresponding to an evolution of this structure resulting in a high damage.

The limit between the first area and the second area may correspond to a particular equivalent ageing (temperature/duration). The limit between the second area and the third area may correspond to another particular equivalent ageing. These values are representative of transformation thresholds which allow establishing the category of the damage.

According to one form of the present disclosure, the polyurethane paint under the commercial designation 5014 is used.

According to other optional features of the method according to the invention:

the wave number of the particular peak is close to 1300/cm, being between 1288 and 1314/cm;

in order to obtain the first criterion, the first trough comprised between 1322 and 1374/cm is considered, and the second trough comprised between 1236 and 1247/cm is considered, the value 1247/cm being retained if this second trough is not pronounced on the curve;

in the case where the particular peak is no longer observable, then the largest height comprised between the base line and the curve is measured between 1288 and 1314/cm, in order to obtain the first criterion which may be negative;

in order to obtain the second criterion, the first significant trough close to 2000/cm, comprised between 1951 and 2051/cm, and the second significant trough close to 1000/cm, comprised between 901 and 1102/cm, are considered;

in the case where the particular peak is no longer observable, then the height between the base line and the curve at the value 1288/cm is measured in order to obtain the second criterion.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 4:
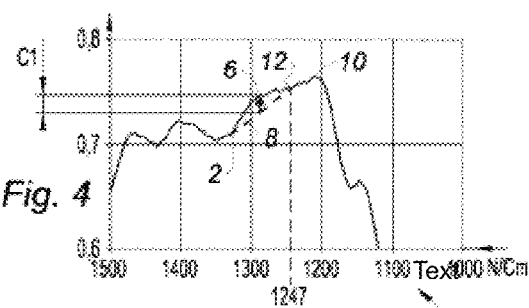
Figure 3:
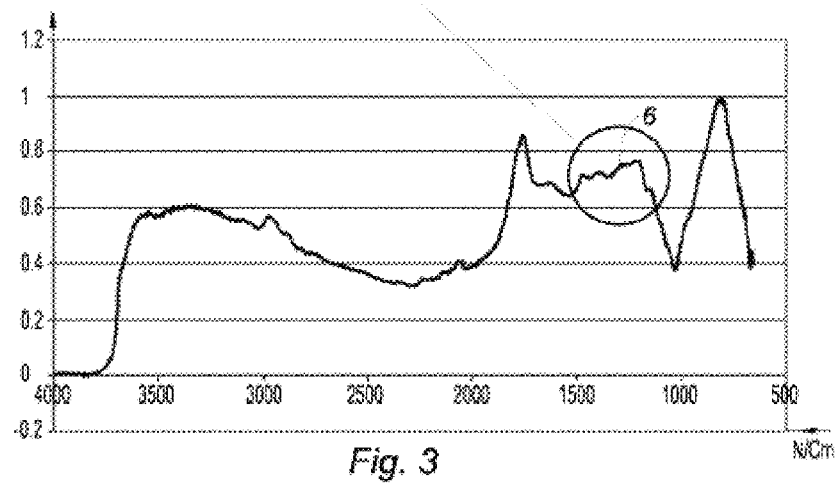
Figure 5:
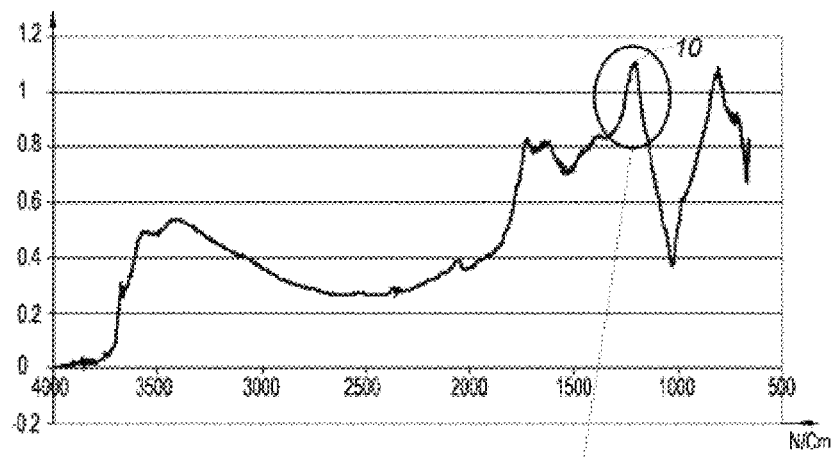
Figure 6:
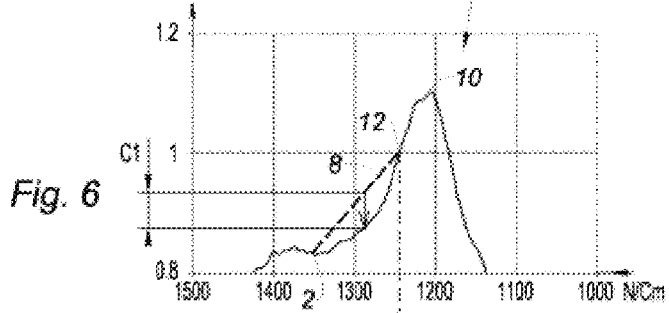
Figure 7:
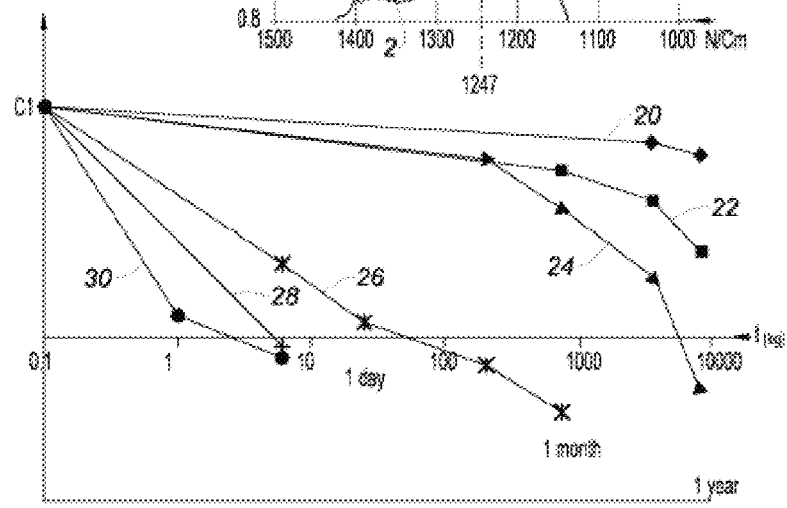
Figure 8:
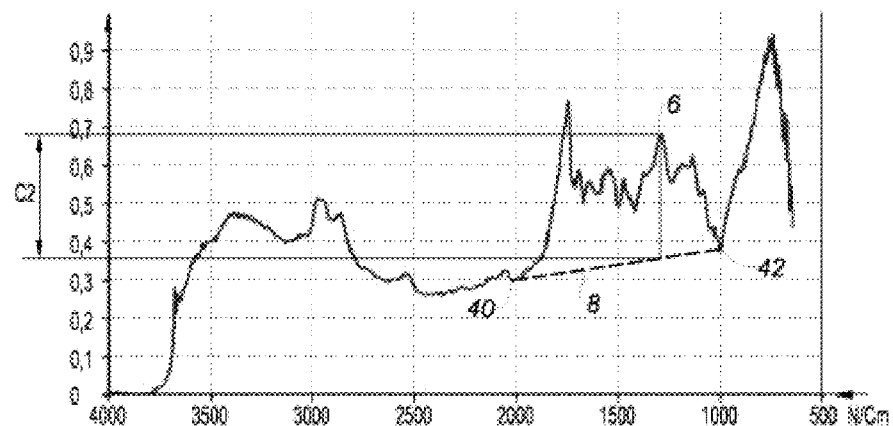
Figure 9:
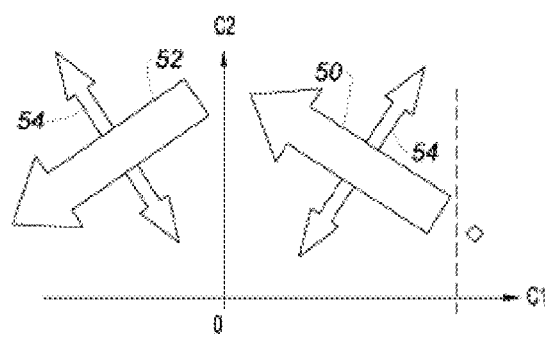
Figure 10:
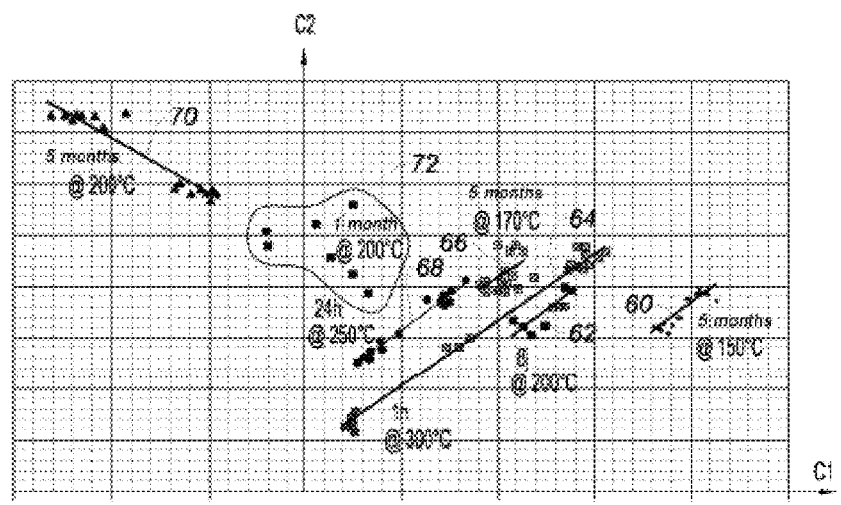

FIGS. 3 and 4 present a method for measuring the first criterion for a dimly visible particular peak;

FIGS. 5 and 6 present a method for measuring the first criterion for a non visible particular peak;

FIG. 7 presents the value of the first criterion as a function of the exposure time of the material and the reached temperature;

FIG. 8 presents a method for measuring the second criterion;

FIG. 9 is a graph presenting the principle of thermal exposure variation as a function of the two criteria; and FIG. 10 is the same graph showing, for identical thermal exposures, measurements for paints including different conditions of implementation.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Figure 1:
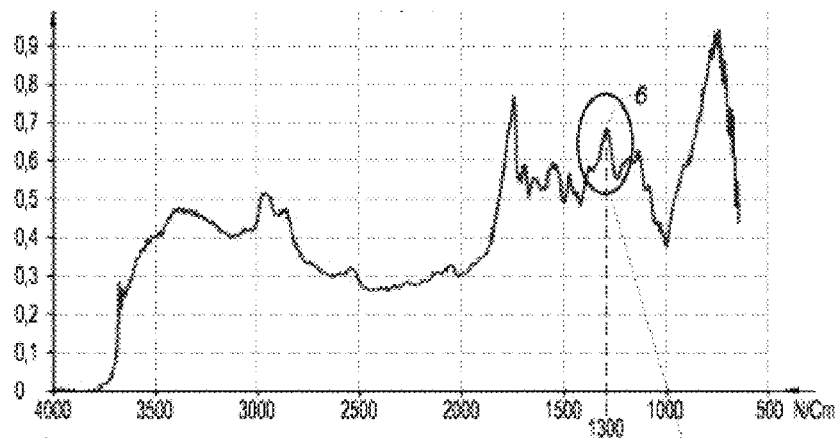
FIG. 1 is an infrared spectrogram obtained for the analysis of a composite material with a method according to the present disclosure.

FIGS. 1 and 8 present, as a function of the wave number per centimeter N/cm, the curve obtained for a spectrometry on a panel made of composite materials and covered with a primary 5014-type polyurethane paint. The measurement is performed for a wave number comprised between 4000 and 650/cm.

It is possible in particular to perform this analysis on parts made of carbon fiber and bismaleimide-type resin ("BMI"), covered with the primary polyurethane.

The obtained spectrum is characteristic of a primary polyurethane paint with this reference, it evolves as a function of temperature exposure, comprising the temperature level and the exposure time.

The spectrometry is carried out with a portable apparatus brought into contact with the part, according to the diffuse reflection technique, adapted to the surface condition of the composite material panel. The surface condition of the part is prepared beforehand through a cleaning with a solvent, in order to eliminate pollution that might disturb the measurements and modify the spectrogram.

From this spectrogram, two different criteria C1 and C2 are identified on the curve in order to characterize the thermal ageing.

The use of two criteria allows obtaining, via a comparison of these criteria, an assessment of the thermal ageing which is independent from the parameters of implementation of the polyurethane paint and from the measurement conditions, thereby making the measurement reliable. It will be noted that the use of one single criterion does not allow any comparison, we remain dependent on the parameters of implementation and on the measurement conditions, which does not give a reliable result.

For the calculation of the first criterion C1 presented in FIG. 1, the height of a particular peak 6 is measured on the spectrogram relative to a base line 8 passing through the first two immediately adjacent troughs 2, 4 on each side of this peak. For the calculation of the second criterion C2 presented in FIG. 8, the height of the particular peak 6 is measured relative to a base line 8 passing through the first two significant troughs 40, 42 on each side of this peak.

It will be noted that the troughs on the curve representing low-emission points which vary slightly during thermal ageing, constitute references allowing to measure the evolution of the height of the peak 6.

In this example with a 5014-type polyurethane primary paint, the particular peak 6 is chosen close to the 1300/cm wave number, being between 1288 and 1314/cm.

Figure 2:
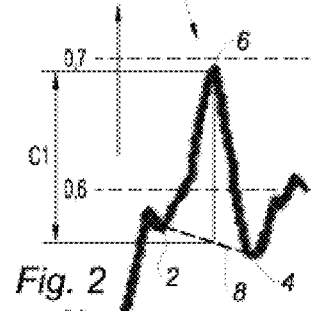
FIG. 2 is a detail view of this spectrogram showing the measurement of a first criterion of this method, for a highly visible particular peak.

FIGS. 1 and 2 present the case of a spectrogram having the particular peak 6 easily observable thanks to a first point 2 corresponding to the trough located just to the left, and to a second point 4 corresponding to the trough located just to the right. Then, the height of this peak 6 is measured relative to the base line 8 connecting the two points 2, 4, in order to obtain the first criterion C1.

FIGS. 3 and 4 present the case of a spectrogram having a particular peak 6 which is reduced through the presence of a second peak 10 located to the right, at about 1200/cm, without the second trough between the particular peak 6 and this second peak 10.

In this case, there is arranged a base line 8 which passes through the first point 2 corresponding to the left trough 2, and through a second point of the curve 12 considered at the value 1247/cm. The height of the particular peak 6 is measured, in the same manner, relative to this base line 8, in order to obtain the second criterion C2.

FIGS. 5 and 6 present the case of a spectrogram having a particular peak 6 which is not observable because of the presence of the second peak 10 located to the right, at about 1200/cm, which is very developed. Then, there is a total absence of troughs at 1250/cm.

In this case, there is also arranged a base line 8 which passes through the first point 2 corresponding to the left trough, and through the second point of the curve 12 considered at the value 1247/cm. Afterwards, the largest height between this base line 8 and the curve, comprised between 1288 and 1314/cm, is measured in order to obtain the first criterion C1. In this example, the height is negative, this first criterion C1 is then negative.

In a general manner for the calculations of the first criterion C1, the base line 8 passes through a first point corresponding to the left trough 2 comprised between 1322 and 1374/cm, and through a second point 4 corresponding to the right trough comprised between 1236 and 1247/cm, or without right troughs through a second point 12 at the value 1247/cm.

FIG. 7 presents, as a function of the exposure time indicated on a logarithmic scale, the value of the first criterion C1 presented on referenced curves 20, 22, 24, 26, 28, 30, respectively corresponding to the temperatures of 100, 150, 170, 200, 250 and 300° C.

It is observed that this first criterion C1 is actually characteristic of thermal ageing, with a variation depending both on the temperature level and on the exposure time.

FIG. 8 presents the calculation of the second criterion C2, which measures the height of the particular peak 6 relative to a base line 8 connecting the first significant trough 40 located to the left at 2000/cm, comprised between 1951 and 2051/cm, to the second significant trough 42 located to the right at 1000/cm, comprised between 901 and 1102/cm.

In the case where the particular peak 6 is no longer observable through the presence of a second peak located to the right at about 1200/cm which is very developed, as presented in FIGS. 5 and 6, then the height between the base line 8 and the curve at the value 1288/cm is measured, in order to obtain the measurement of the second criterion C2.

FIG. 9 presents a graph comprising the first criterion C1 on a horizontal axis and the second criterion C2 on a vertical axis, on which the measured criteria of the material to be analyzed are disposed.

Through their path, the main arrows 50 then 52 present a modification of the two criteria C1, C2 giving a more and more significant thermal exposure, whether by the higher temperature level that has been reached or by the longer exposure time, which will give a more and more significant degradation of the material.

In contrast, along their directions, the transverse arrows 54 present a modification of the two criteria C1, C2 corresponding to a variation of the parameters of implementation of the polyurethane paint or of the surface conditions, which do not displace the points along the direction of the main arrows 50, 52, which gives a similar thermal degradation of the material.

FIG. 10 presents, on the same graph, different measurements which confirm the principle presented above. Each set of measurements groups, substantially around an axis with a constant slope, aligned along the directions of the transverse arrows 54, a set of points corresponding to the same thermal ageing, on a polyurethane paint implemented under different conditions.

In particular, there is a first axis 60 corresponding to an temperature exposure of 150° C. for five months, a second axis 62 corresponding to 200° C. for eight days, a third axis 64 corresponding to 300° C. for one hour, a fourth axis 66 corresponding to 170° C. for five months, a fifth axis 68 corresponding to 250° C. for twenty-four hours, and a sixth axis 70 corresponding to 200° C. for five months. There is also a group of points 72 corresponding to 200° C. for one month, which is located proximate to the first criterion C1 equal to zero.

Thus, is obtained in a simple and rapid manner, without destruction of the material, an accurate assessment of the thermal engagement level of the materials which is independent from the parameters of implementation of the primary paint, and from the measurement conditions.

What is claimed is:

1. A method for assessing damage to a composite material covered with a polyurethane-type paint comprising: bringing an apparatus into contact with the composite material, measuring two separate criteria on a same spectrogram obtained by infrared spectrometry, thereby characterizing thermal ageing of the paint, each separate criteria comprising a measurement on a curve of a spectrum of the same spectrogram of a height of a particular peak, thereby giving two independent assessments of the thermal ageing and combining the two separate criteria to obtain a result of a level of the damage to the composite material without destruction of the composite material.

2. The assessment method according to claim 1, wherein in order to obtain a first criterion of the two separate criteria, the height of the particular peak is measured relative to a base line passing through a first two immediately adjacent troughs on each side of the peak.

3. The assessment method according to claim 1, wherein in order to obtain a second criterion of the two separate criteria, the height of the particular peak is measured relative to a base line passing through a first two significant troughs on each side of the peak.

4. The assessment method according to claim 1, wherein the two separate criteria are disposed along two axes of a graph in order to determine a level of thermal degradation of the composite material.

5. The method according to claim 1, wherein a wave number of the particular peak is about 1300/cm.

6. The method according to claim 5, wherein a wave number of the particular peak is between 1288 and 1314/cm.

7. The assessment method according to claim 5, wherein in order to obtain a first criterion of the two separate criteria, the height of the particular peak is measured relative to a base line passing through a first two immediately adjacent troughs on each side of the peak, and in order to obtain the first criterion, a first trough of one of the adjacent troughs between 1322 and 1374/cm is considered, and a second trough of the adjacent troughs between 1236 and 1247/cm is considered, the value 1247/cm being retained if the second trough is not pronounced on the curve.

8. The assessment method according to claim 5, wherein in order to obtain a first criterion of the two separate criteria, the height of the particular peak is measured relative to a base line passing through a first two immediately adjacent troughs on each side of the peak, and in a case where the particular peak is no longer observable, a largest height between the base line and the curve is measured between 1288 and 1314/cm, in order to obtain the first criterion that is negative.

9. The assessment method according to claim 5, wherein in order to obtain a second criterion of the two separate criteria, the height of the particular peak is measured relative to a base line passing through a first two significant troughs on each side of the peak, and in order to obtain the second criterion, a first significant trough between 1951 and 2051/cm and a second significant trough between 901 and 1102/cm are considered.

10. The assessment method according to claim 9, wherein in a case where the particular peak is no longer observable, then a height between the base line and the curve at a 1288/cm value is measured, in order to obtain the second criterion.

* * * * *